(12) United States Patent
Dominguez et al.

(10) Patent No.: US 9,895,246 B2
(45) Date of Patent: Feb. 20, 2018

(54) REACTIVE INTRAGASTRIC IMPLANT DEVICES

(71) Applicant: Apollo Endosurgery, Inc., Austin, TX (US)

(72) Inventors: Zachary Dominguez, Santa Barbara, CA (US); Justin Schwab, Santa Barbara, CA (US); Mitchell H. Babkes, Santa Clarita, CA (US)

(73) Assignee: Apollo Endosurgery US, Inc., Austin, TX (US)

( * ) Notice: Subject to any disclaimer, the term of this patent is extended or adjusted under 35 U.S.C. 154(b) by 180 days.

(21) Appl. No.: 14/621,094

(22) Filed: Feb. 12, 2015

(65) Prior Publication Data

US 2015/0150700 A1    Jun. 4, 2015

Related U.S. Application Data

(62) Division of application No. 13/276,182, filed on Oct. 18, 2011, now Pat. No. 8,956,380.

(60) Provisional application No. 61/394,708, filed on Oct. 19, 2010, provisional application No. 61/394,592, filed on Oct. 19, 2010, provisional application No. 61/394,145, filed on Oct. 18, 2010.

(51) Int. Cl.
*A61F 5/00*    (2006.01)

(52) U.S. Cl.
CPC .......... *A61F 5/0033* (2013.01); *A61F 5/0036* (2013.01)

(58) Field of Classification Search
CPC ........ A61B 17/12022; A61B 17/12027; A61B 17/12036; A61B 17/1204; A61B 17/12163; A61B 5/6871; A61M 29/00; A61F 5/003; A61F 5/0033
See application file for complete search history.

(56) References Cited

U.S. PATENT DOCUMENTS

| | | | | |
|---|---|---|---|---|
| 563,170 | A * | 6/1896 | Haley et al. | A63B 43/002 473/595 |
| 4,739,758 | A * | 4/1988 | Lai | A61F 5/0036 604/909 |
| 2007/0118168 | A1 * | 5/2007 | Lointier | A61F 5/003 606/192 |
| 2008/0243221 | A1 * | 10/2008 | Arcand | A61F 2/958 623/1.11 |
| 2009/0171382 | A1 * | 7/2009 | Dillon | A61F 5/0036 606/192 |
| 2013/0190664 | A1 * | 7/2013 | Johnson | A61H 15/0092 601/129 |

* cited by examiner

*Primary Examiner* — Thomas McEvoy
(74) *Attorney, Agent, or Firm* — Gordon & Jacobson, P.C.

(57) ABSTRACT

Transoral implantable devices includes an inflatable body made of a material that permits it to be compressed into a substantially linear transoral delivery configuration and that when implanted in the stomach is adapted to reduce obesity or weight by stimulating the stomach walls of the patient. The body has a plurality of popout features on its surface that reside generally flush with the inflatable body in relaxed, refracted states, and which respond to an increase in pressure within the inflatable body by projecting outward from the body in a stressed, deployed state. The popout features may convert between their retracted and deployed states by movement of rolling diaphragms formed in the inflatable body.

17 Claims, 11 Drawing Sheets

REACTIVE INTRAGASTRIC IMPLANT DEVICES

RELATED APPLICATIONS

This application is a divisional of U.S. Ser. No. 13/276,182, filed Oct. 18, 2011, which claims priority under 35 U.S.C. § 119(e) to U.S. Provisional Application No. 61/394,708, filed Oct. 19, 2010, to U.S. Provisional Application No. 61/394,592, filed Oct. 19, 2010, and to U.S. Provisional Application No. 61/394,145, filed Oct. 18, 2010, the disclosures of which are incorporated by reference herein.

FIELD OF THE INVENTION

The present invention generally relates to medical implants and uses thereof for treating obesity and/or obesity-related diseases and, more specifically, to transorally-delivered devices designed to occupy space within a stomach and/or stimulate the stomach wall and react to changing conditions within the stomach.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States was estimated to be about 400,000 in 2010.

Examples of surgical methods and devices used to treat obesity include the LAP-BAND® (Allergan Medical of Irvine, Calif.) gastric band and the LAP-BAND AP® (Allergan). However, surgery might not be an option for every obese individual; for certain patients, non-surgical therapies or minimal-surgery options are more effective or appropriate.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These devices are designed to provide therapy for moderately obese individuals who need to shed pounds in preparation for surgery, or as part of a dietary or behavioral modification program. These balloons are typically cylindrical or pear-shaped, generally range in size from 200-500 ml or more, are made of an elastomer such as silicone, polyurethane, or latex, and are filled with air, an inert gas, water, or saline.

One such inflatable intragastric balloon is described in U.S. Pat. No. 5,084,061 and is commercially available as the BioEnterics Intragastric Balloon System ("BIB System," sold under the trademark ORBERA). The BIB System comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Placement of such balloons is temporary, and such balloons are typically removed after about six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Some attempted solutions for weight loss by placing devices in the stomach result in unintended consequences. For instance, some devices tend to cause food and liquid to back up in the stomach, leading to symptoms of gastroesophageal reflux disease (GERD), a condition in which the stomach contents (food or liquid) leak backwards from the stomach into the esophagus. Also, the stomach acclimates to some gastric implant devices, leading to an expansion of stomach volume and consequent reduction in the efficacy of the device.

Therefore, despite many advances in the design of intragastric obesity treatment implants, there remains a need for improved devices that can be implanted for longer periods than before or otherwise address certain drawbacks of intragastric balloons and other such implants.

SUMMARY OF THE INVENTION

Transoral three-dimensionally orthogonal intragastric spring devices generally promote a feeling of satiety in the patient by contacting the insides of the stomach wall. In addition, transoral three-dimensionally orthogonal intragastric spring devices generally allow for easy and quick placement and removal. Surgery is usually not required or very minimal. In one embodiment, the transoral three-dimensionally orthogonal intragastric spring devices may be placed in the patient's stomach through the mouth, passing the esophagus and reaching the destination. The transoral three-dimensionally orthogonal intragastric spring devices do not require suturing or stapling to the esophageal or stomach wall, and remains inside the patient's body for a lengthy period of time (e.g., months or years) before removal.

Each of the disclosed devices is formed of materials that will resist degradation over a period of at least six months within the stomach. The implantable devices are configured to be compressed into a substantially linear transoral delivery configuration and placed in a patient's stomach transorally without surgery to treat and prevent obesity by applying a pressure to the patient's stomach.

In one embodiment, a transoral three-dimensionally orthogonal intragastric spring device may fight obesity or reduce weight by stimulating the stomach walls of the patient. The three-dimensionally orthogonal intragastric spring device may be a purely mechanical device comprising a flexible body which in response to an input force in one direction, may deform and cause a resultant displacement in an orthogonal direction, thereby exerting a pressure on the inner stomach walls of the patient.

In another embodiment, a transoral three-dimensionally orthogonal intragastric spring device may include a variable size balloon. The balloon may be configured to occupy volume in the patient's stomach, thereby reducing the amount of space in the patient's stomach.

In a particular embodiment disclosed herein, a reactive implantable device comprises a three-dimensional spring structure comprising a plurality of legs each having opposite ends extended between top and bottom junctions of the spring structure defining an axis. Each leg has a flexible portion and a rigid portion attached to the flexible portion, wherein the flexible portions of each leg has a relaxed shape which causes the leg to bow laterally outward from the other legs thus maintaining the top and bottom junctions at a first distance apart. The implantable device is configured to react to inward forces from the stomach such that the flexible portions flex to straighten each leg and cause the axial spacing between the top and bottom junctions to increase from the first distance. The implantable device may have four or more legs, and the rigid portion comprises four or more distinct rigid members per leg. Each of the top and bottom junctions preferably comprises a quadrilateral-shaped cap, wherein the opposite ends of each leg are attached to different edges of the respective quadrilateral-shaped caps.

In one embodiment, a balloon is integrated with the three-dimensional spring structure and filled with fluid. The balloon may be within or outside the legs of the three-dimensional spring structure. If outside, the device may further include a pump located within the balloon and integrated with the three-dimensional spring structure configured to inflate and deflate the elastic balloon by transferring stomach liquid into and out of the elastic balloon.

Another reactive implantable device disclosed herein comprises a central elongated body having an adjustable length. Two collapsible atraumatic feet on opposite ends of the elongated body are configured to exert pressure on the patient's stomach when in a deployed position. A spring within the central elongated body biases the length of the body away from a minimum length. The two collapsible atraumatic feet may comprise balloon-like structures. The two collapsible atraumatic feet may alternatively comprise an array of living hinges that may be unfolded to an elongated delivery configuration and folded outward to a deployed configuration. In one embodiment, the array of living hinges is in an X-shape. The central elongated body preferably comprises a series of telescoping tubular members having apertures along their lengths.

A still further reactive implantable device includes an inflatable body having an internal volumetric capacity of between 400-700 ml and being made of a material that permits it to be compressed into a substantially linear transoral delivery configuration and that will resist degradation over a period of at least six months within the stomach. The body has a plurality of popout features on its surface that reside generally flush with the inflatable body in relaxed, retracted states, and which respond to an increase in pressure within the inflatable body by projecting outward from the body in a stressed, deployed state. The inflatable body may have a generally barrel shape along an axis. The popout features may be generally cylindrical, or are rounded bars oriented parallel to the axis. The popout features preferably convert between their retracted and deployed states by movement of rolling diaphragms formed in the inflatable body.

A still further reactive implantable device disclosed herein has an inflatable body with an internal volumetric capacity of between 400-700 ml and being made of a material that permits it to be compressed into a substantially linear transoral delivery configuration and that will resist degradation over a period of at least six months within the stomach. The body has a central inflatable member and at least two outer wings, and a single internal fluid chamber such that fluid may flow between the central inflatable member and the outer wings. The inflatable body is underfilled with fluid such that the outer wings are floppy in the absence of compressive stress on the central inflatable member and stiff when compressive stress from the stomach acts on the central inflatable member. The central inflatable member may have a generally spherical shape along an axis. There are preferably two outer wings extending in opposite directions from the generally spherical inflatable member along the axis. In one form, each of the outer wings includes a narrow shaft portion connected to the central inflatable member terminating in bulbous heads.

The invention also comprises a reactive implantable device configured for transoral placement into a patient's stomach for the treatment of obesity by applying a pressure to the patient's stomach, the implantable device comprising: a spring or spring type structure having a plurality of legs each leg having opposite ends extended between top and bottom junctions of the spring thereby defining an axis, each leg also having a flexible portion and a rigid portion attached to the flexible portion, wherein the flexible portions of each leg has a relaxed shape which causes the leg to bow laterally outward from the other legs to thereby maintain the top and bottom junctions at a first distance apart, and wherein the implantable device is configured to react to inward forces from the stomach such that the flexible portions flex to straighten each leg and cause the axial spacing between the top and bottom junctions to increase from the first distance, wherein the device is formed of materials that permit it to be compressed into a substantially linear transoral delivery configuration and that will resist substantially resist degradation over a period of at least six months within the stomach. To substantially resist degradation means that when placed in the acid environment of the stomach the device still functions at least substantially as intended, that is a clinically significant result (i.e. weight loss or the maintenance of a weight loss) can still be obtained.

BRIEF DESCRIPTION OF THE DRAWINGS

The following detailed descriptions are given by way of example, but not intended to limit the scope of the disclosure solely to the specific embodiments described herein, may best be understood in conjunction with the accompanying drawings in which:

FIGS. 9A-9C are perspective and sectional views of an alternative reactive intragastric implant comprising a generally barrel-shaped inflatable member having "pop-out" surface features in refracted positions, while

FIGS. 12A-12C are perspective and sectional views of a further barrel-shaped inflatable intragastric implant having elongated "pop-out" surface features in retracted positions, while

DESCRIPTION OF THE DETAILED EMBODIMENTS

Figure 1:
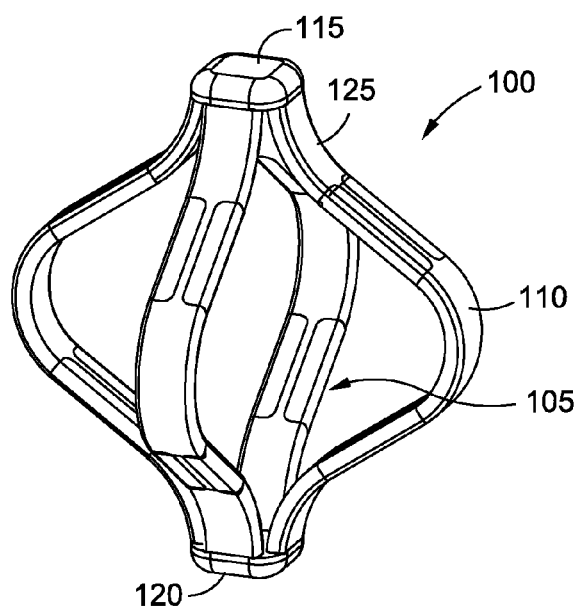
FIG. 1 illustrates a perspective view of a reactive intragastric implant comprising a three-dimensionally orthogonal intragastric spring device in accordance with one or more embodiments described herein.

Persons skilled in the art will readily appreciate that various aspects of the disclosure may be realized by any number of methods and devices configured to perform the intended functions. Stated differently, other methods and devices may be incorporated herein to perform the intended functions. It should also be noted that the drawing FIGS. referred to herein are not all drawn to scale, but may be exaggerated to illustrate various aspects of the invention, and in that regard, the drawing FIGS. should not be construed as limiting. Finally, although the present disclosure may be described in connection with various medical principles and beliefs, the present disclosure should not be bound by theory.

By way of example, the present disclosure will reference certain transoral three-dimensionally orthogonal intragastric spring device. Nevertheless, persons skilled in the art will readily appreciate that the present disclosure advantageously may be applied to one of the numerous varieties of three-dimensionally orthogonal intragastric spring devices.

In one embodiment, these three-dimensionally orthogonal intragastric spring device described herein are intended to be placed inside the patient, transorally and without invasive surgery, without associated patient risks of invasive surgery and without substantial patient discomfort. Recovery time may be minimal as no extensive tissue healing is required. The life span of these transoral three-dimensionally orthogonal intragastric spring devices may be material-dependent upon long-term survivability within an acidic stomach, but is intended to last one year or longer.

FIG. 1 illustrates one embodiment of a transoral three-dimensionally orthogonal intragastric spring device, namely spring device 100. The spring device 100 features a plurality of legs 125 having opposite ends extending between upper and lower junctions 115, 120. The legs 125 each include rigid portions 105 integrated with flexible or elastic portions 110. The elastic portions 110 extend the entire length of the legs 125 and essentially form the legs, with the rigid portions 105 being embedded or otherwise intimately attached thereto. In the illustrated embodiment, the spring device 100 has two rigid portions 105 for every leg 125. More particularly, one rigid portion 105 may be embedded within the flexible portions 110 in the top half of the leg 125, and a second rigid portion 105 may be embedded within the flexible portions 110 of the second half of the leg 125. In one embodiment, the rigid portions 105 have substantially the same thickness as the flexible portion 110, and extend a short distance along each leg. As there are four legs 125 shown, a total of eight rigid portions 105 may be included in this embodiment of the spring device 100. The elastic portion 110 of each leg 125 primarily controls the bending flexibility of the leg, while the rigid portions 105 contribute rigidity to certain areas. In the illustrated configuration, therefore, the flexible portions 110 are relatively unconstrained at their top and bottom ends, and in a middle section between the upper and lower rigid portions 105.

The legs 125 are attached and held together by the top and bottom junctions 115 and 120, respectively. The junctions 115, 120 desirably comprise top and bottom caps. As shown, the caps forming the junctions 115 and 120 are quadrilateral in configuration and each leg 125 attaches to a different one of the four sides of the caps 115 and 120. As shown, the spring device 100 is in a natural state and fully functional. That is, the shape shown in FIG. 1 is the relaxed shape of the device 100, with the elastic portions 110 of each leg 125 in equilibrium and not under any bending stress.

In one embodiment, the materials used to construct the spring device 100 may include metals, thermoplastics, thermoplastic elastomers, silicones, glass, thermosets or any combination thereof. More particularly, the rigid portions 105 may be made of a more rigid material such as a silver alloy or glass, while the flexible portions 110 may be constructed out of elastomeric materials. If silver is used, the rigid portions 105 provide an antiseptic benefit to the device 100 to prevent bacteria from growing. The junction caps 115 and 120 may also be constructed out of rigid materials. In one embodiment, the flexible portions 110 may be constructed out of one material, while the rigid portions 120 and the junction caps, 115 and 120, are constructed out of a second material.

Figure 2A:
FIG. 2A illustrates a rigid member of a three-dimensionally orthogonal intragastric spring device as in FIG. 1.

In the embodiment illustrated in FIGS. 2A-2D, each rigid portion 105 comprises a pair of rigid strips 205 embedded within or otherwise secured along the corresponding flexible portion 210. A single rigid portion 205 is shown in FIG. 2A. Each rigid portion 205 appears as parallel, unattached strips that attach in parallel pairs along opposite circumferential sides of the host flexible portion 210. Preferably, the rigid portions 205 are substantially unbendable and inflexible, though such terms are relative. Alternatively, the rigid portions 205 may still have elastic qualities, but might not be as elastic or flexible as the rest of the spring device 200, and in particular, the flexible portions 210. For instance, if the flexible portions 210 are formed of an elastomer, such as silicone, then the rigid portions 205 could be silver or glass, both of which are relatively less flexible, though silver bends under the influence of greater forces and glass will eventually crack due to its brittle nature. However, if glass is used the small size of each rigid portion 205 and relatively low bending stresses imparted thereto ensures a high degree of confidence that the glass will not break. Ceramic is another option.

Figure 2B:
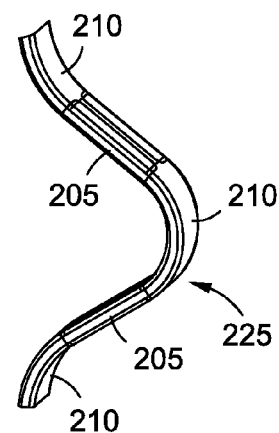
FIG. 2B illustrates a rigid member molded to the three-dimensionally orthogonal intragastric spring device of FIG. 1.
Figure 2C:
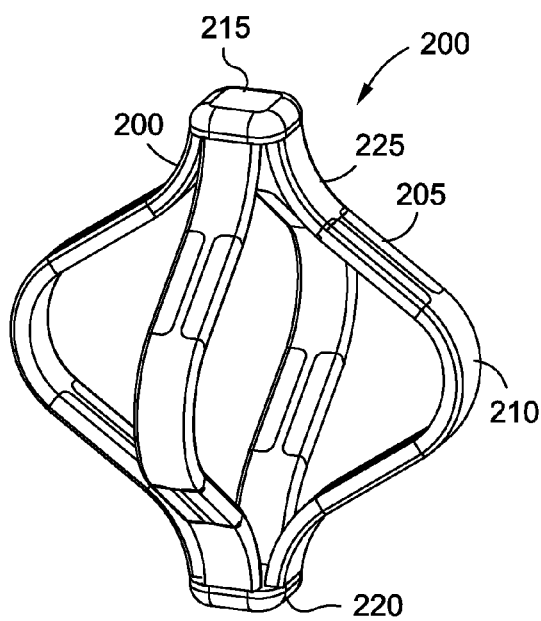
FIG. 2C illustrates an uncapped three-dimensionally orthogonal intragastric spring device of FIG. 1.

FIG. 2B shows the rigid portion 205 attached or molded to the flexible portion 210, thus forming a leg 225. As shown, the leg 225 may flex at any of the purely flexible portions 210, but are less flexible along the rigid portions 205. In one embodiment, between the parallel rigid portions 205 is a portion of the flexible portion 210. In other words, the flexible portion 210 of the leg may constructed as one piece, whereas the rigid portions 205 may be constructed separately and molded to the flexible portion 210. FIG. 2C illustrates four legs 225 arranged uniformly with top and bottom caps. When the caps are attached, the spring device 200 is complete, and may appear similar to the spring device 100.

Figure 2D:
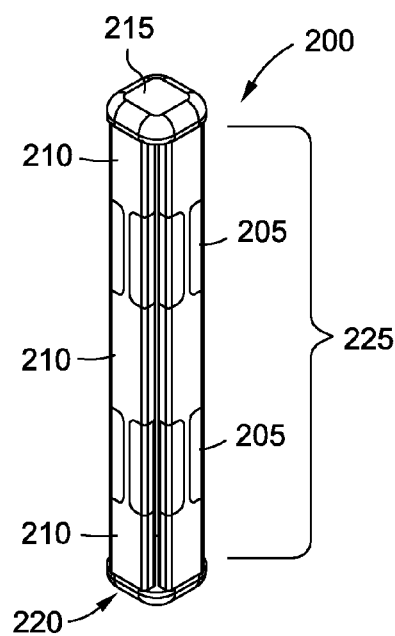
FIG. 2D illustrates a three-dimensionally orthogonal intragastric spring device as in FIG. 1 in a deformed geometry.

FIG. 2D illustrates the spring device 200 with caps (e.g., top and bottom junction caps 215 and 220) holding the legs 225 attached in place. Here, FIG. 2D illustrates the spring device 200 in a deformed, stressed, or straightened state. As shown, the flexible portions 210 are no longer in a curved configuration (e.g., in a natural, relaxed state), but instead is shown in a relatively straightened position. The rigid portions 205 are still substantially flat, similar to the rigid portions as shown in FIGS. 2A-2C. Overall, the spring device 200, is flat and elongated (e.g., the distance between junction caps 215 and 220 is extended when compared to the distance between junction caps 215 and 220 in the configuration of FIG. 2C). Accordingly, this position is advantageous for inserting the spring device 200 through a patient's mouth, down the esophagus and into the patient's stomach, and can be maintained within a delivery tube, for example.

Next, a method of manufacturing of a spring device (e.g., spring device 100 or 200) will be discussed. While the following description refers to spring device 100 specifically, the same principles apply to spring device 200 or any other embodiment of the spring device equally.

Figure 3:
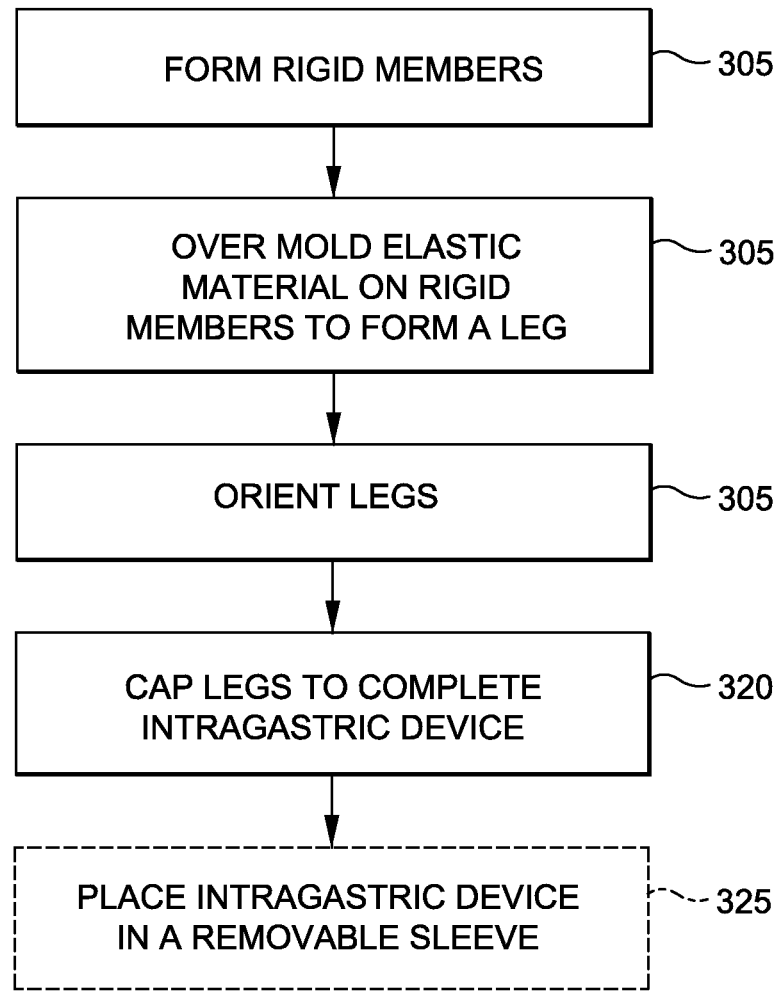
FIG. 3 illustrates a flow diagram describing the steps of manufacture of a three-dimensionally orthogonal intragastric spring device in accordance with one or more embodiments described herein.

FIG. 3 illustrates a method of manufacturing a spring device 100. At step 305, the rigid portions or members 105 may be initially formed. At step 310, elastic material is overmolded on the rigid members 105. The elastic material may comprise the flexible portions 110, and the resulting component of the rigid members 105 with the elastic material may be considered a leg 125. After a plurality of legs are constructed (e.g., four legs as shown in FIG. 1, but any number of legs of 2 or more may be constructed—such as 3 legs, 5 legs, 6 legs, etc.), the legs 125 may be oriented to be evenly spaced apart at step 315. At step 320, the legs 125 may be coupled by a top cap 115 and a bottom cap 120. The ends of the legs 125 may be glued into the caps 115, 120, heat bonded, secured with fasteners, etc. In one embodiment, the caps 115, 120 are crimped onto the ends of the legs 125. In one aspect, the top and bottom junction caps 115 and 120 have a number of edges equal to the number of legs. For example, as shown in FIG. 1, the top and bottom junction caps, 115 and 120, have 4 edges each, one for each of the legs 125.

After formation, and well before or just prior to use, the spring device 100 may be placed inside a removable sleeve, band, or otherwise held in a "deformed" or straightened position (e.g., as shown in FIG. 2D), at step 325, and in this position, the spring device 100 may be ready for insertion into the patient's stomach. In one embodiment, the sleeve or band holding the spring device 100 in a straightened position may be configured to be removable by a standard grabber. For example, the band may have a "snap-on" buckle that is releasable by using a standard grabber to press on a certain portion of the buckle. Alternatively, the sleeve or band may be constructed out of a non-toxic, digestible substance, such as a food or other commonly edible substance like a sugar, so that the sleeve or band may be "removed" by the natural acids inside the patient's stomach after insertion by the patient's natural digestion process. As a result of the digestion of the sleeve or band, the spring device 100 may revert back to an unfolded, compressed configuration (e.g., as shown in FIG. 1). In other words, the sleeve or band acts to decompress and elongate the spring device (e.g., spring device 100 or 200), and the removal of the sleeve or band causes the spring device to contract.

For removal, a standard grabber may encircle the spring device 100 at the flexible portions 110 and decompress the spring device into a straightened state for easy removal. In one embodiment, the flexible portions 110 configured to be "grabbed" by the standard grabber to decompress the spring device 100 may be injected with a radio opaque additive during the construction of these portions so that the physician may identify and view these portions when viewing an x-ray during the removal procedure.

Figure 4A:
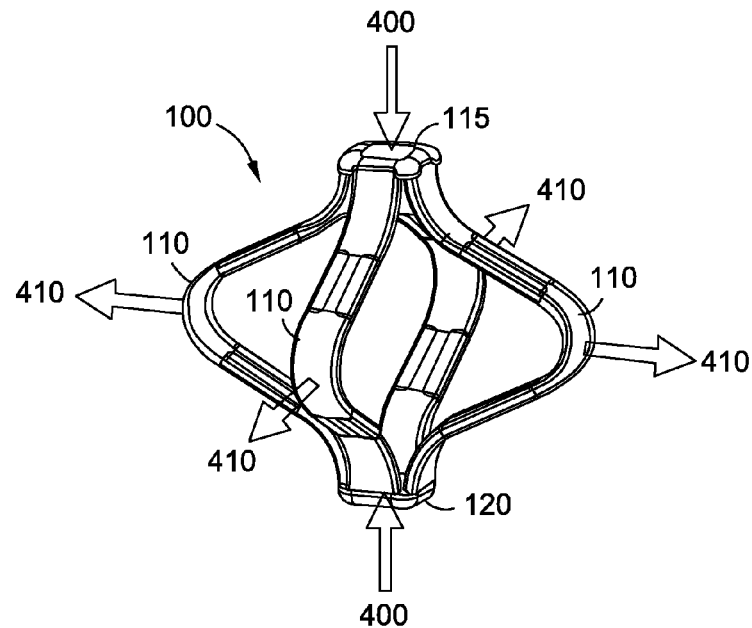
FIG. 4A illustrates a three-dimensionally orthogonal intragastric spring device as in FIG. 1 with input forces in a first direction and the resultant displacement.
Figure 4B:
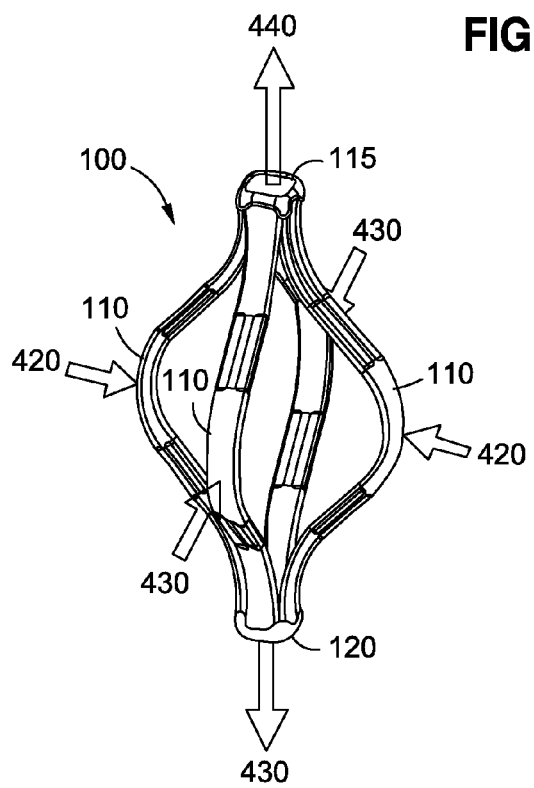
FIG. 4B illustrates a three-dimensionally orthogonal intragastric spring device as in FIG. 1 with input forces in a second direction and the resultant displacement.
Figure 4C:
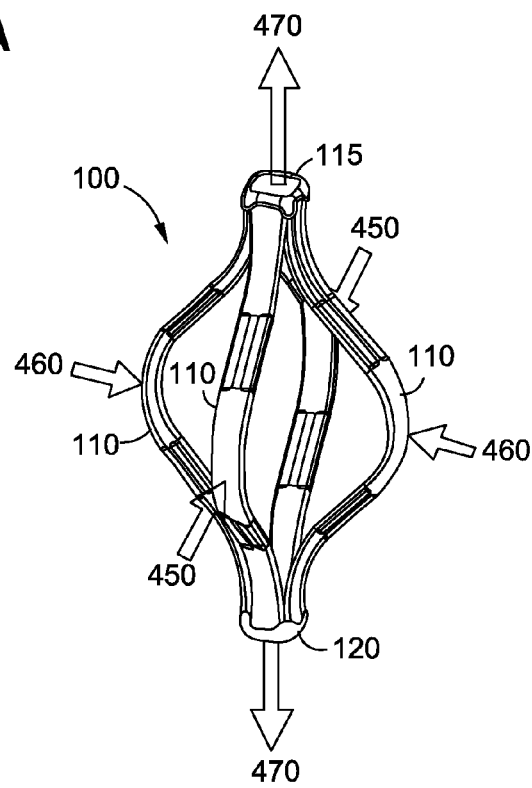
FIG. 4C illustrates a three-dimensionally orthogonal intragastric spring device as in FIG. 1 with input forces in a third direction and the resultant displacement.

Turning to FIGS. 4A-4C, the operation of the spring device 100 deployed inside the patient's stomach will be discussed. Initially, the spring device 100 may reside in the patient's stomach in the configuration as shown in FIG. 1. As the spring device 100 begins to migrate about the patient's stomach due to stomach contractions and/or the patient's position (e.g., the patient is sitting down, lying down, etc.), the spring device 100 may begin to variably rotate and may exert pressure on the patient's stomach in some positions, while not exerting pressure on the patient's stomach in other positions.

FIG. 4A illustrates the spring device 100 where axial compression is exerted on the spring device 100 at the location of the junction caps 115 and 120 (as shown by arrows 400). The pressure exerted by the stomach walls as shown by arrows 400 causes the flexible portions 110 to flex outwards, away from one another, and as a result, the flexible portions 110 pressure the stomach walls in a direction shown by arrows 410.

In another embodiment, as shown by FIG. 4B, when lateral compression is exerted on the spring device 100 at the location of the flexible portions 110 (as shown by arrows 420) by the stomach walls contracting, other flexible portions 110 may also compress (as shown by arrows 430) and, as a result, the junction caps 115 and 120 of the spring device 100 move axially outwards in a direction shown by arrows 440 causing pressure on a different portion of the stomach walls.

Similarly, as shown by FIG. 4C, when lateral compression is exerted on the spring device 100 at the location of the flexible portions 110 (as shown by arrows 450) by the stomach walls contracting, other flexible portions 110 may also compress (as shown by arrows 460) and, as a result, the junction caps 115 and 120 of the spring device 100 move axially outwards in a direction shown by arrows 470 causing pressure on a different portion of the stomach walls.

As described above with respect to FIGS. 4A-4C, an input pressure exerted on the spring device 100 by the inner stomach wall may result in an output pressure exerted by the spring device 100 on the inner stomach wall at a location orthogonal to the location of the input pressure. Moreover, as the spring device 100 rotates and moves around variably within the patient's stomach, the spring device 100 may occupy different three-dimensional space areas within the patient's stomach and may also contact and exert a pressure on the patient's stomach in any of a number of different locations of the inner stomach wall. In this fashion, the spring device 100 limits the ability of the stomach to adapt over long term implantation.

Figure 5A:
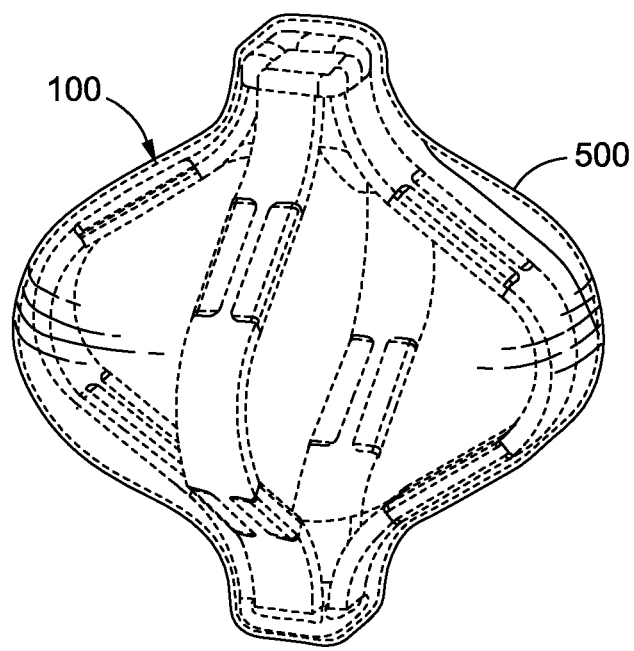
FIG. 5A illustrates a three-dimensionally orthogonal intragastric spring device with an external intragastric balloon in accordance with one or more embodiments described herein.
Figure 5B:
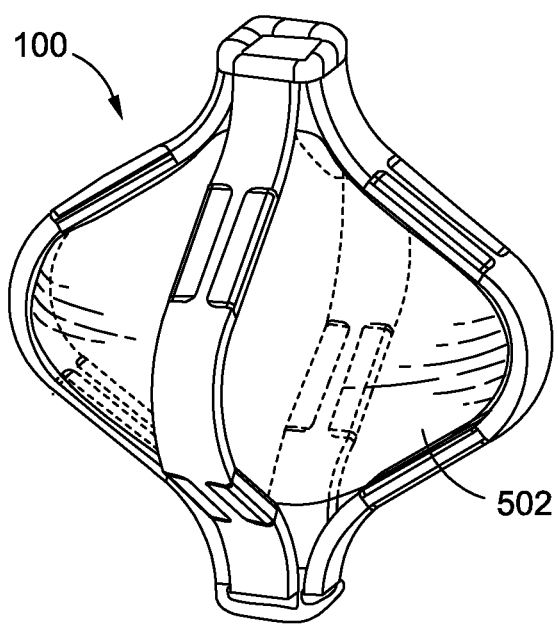
FIG. 5B illustrates a three-dimensionally orthogonal intragastric spring device with an internal intragastric balloon in accordance with one or more embodiments described herein.

In different embodiments, the spring device (e.g., spring device 100 or 200) may further include an intragastric balloon. FIGS. 5A and 5B illustrate two examples of such embodiments. FIG. 5A is an example of an embodiment with an external intragastric balloon 500 surrounding the spring device 100. Alternatively, as shown in FIG. 5B, an internal intragastric balloon 502 may be located inside the legs 125 of spring device 100. Here, the intragastric balloon 502 may be held in place inside the spring device 100 by the particular configuration of the legs 125. By utilizing an intragastric balloon (e.g., 500 or 502), the spring device 100 may also act as an effective volume occupying device inside the patient's stomach, thereby reducing the amount of space inside the patient's stomach to hold food. The balloons are desirably saline-filled.

Figure 6:
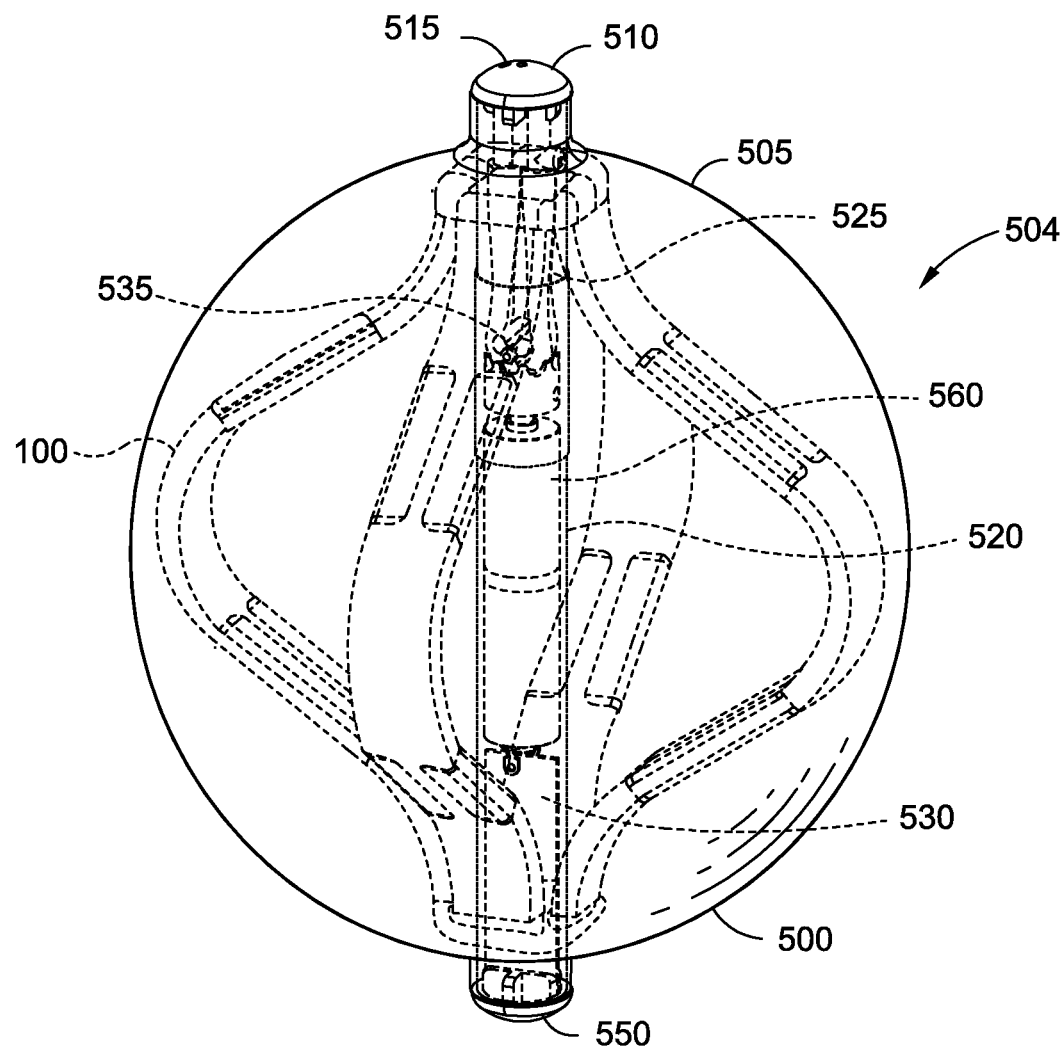
FIG. 6 illustrates a perspective view of another embodiment of the three-dimensionally orthogonal intragastric spring device as in FIG. 1 with a variable size external balloon inflated.

FIG. 6 illustrates another embodiment of a transoral device 504 comprising an external gastric balloon 500 in conjunction with the spring device 100. Legs of the spring device 100 desirably attach and/or are integrated into a central tubular body 520 of the intragastric balloon 500. For instance, the aforementioned end caps may be rigidly integrated into the tubular body 520. As shown, the intragastric balloon 500 may comprise a "balloon" layer 505; that is the balloon 500 may not extend completely around but may be open at opposite poles for passage of the body 520.

In one embodiment, the transoral device 504 may be considered a two-phase intragastric device. In the first phase, the intragastric balloon 500 expands to a sufficient volume that effectively negates the impact of the spring device 100. That is, the intragastric balloon 500 may be so large that the legs of spring device 100 never contact the inside of the stomach walls. In this phase, the spring device 100 is a purely volume occupying device. In a second phase, the volume of the intragastric balloon 500 is reduced (deflated) such that the legs of the spring device 100 protrude against the "walls" or balloon layer 505 of the intragastric balloon 500, thereby receiving input pressures from the stomach walls during contraction, and causing the spring device 100 to react as described above with respect to FIGS. 4A-4C. In this second phase, the transoral device may be both a volume occupying device and an inner wall stimulating device. Since the volume of the intragastric balloon 500 may be controlled according to a schedule and/or externally by a physician, either the first or second phase may be selected in order to best assist the patient to lose weight based on the time of day or in relationship to the patient consuming food. For example, during meals, it may be more beneficial to stimulate the stomach walls and thus, phase two may be more appropriate, but between meals, it may be more beneficial just to have a larger volume occupied in the stomach and thus, phase one may be more appropriate. In one embodiment, the transoral device 504 may be configured to move from a first phase to a second phase, back to the first phase, etc. according to a schedule or other trigger.

The inflatable balloon device 504 may be inflated and filled with stomach juices naturally occurring and produced in the patient's body. At the outer surface of the top 510 of the central tubular body 520 is an opening 515 that functions as an intake for a peristaltic pump 525 integrated into the body 520. The pump 525 pulls stomach juices into the inflatable layer 505 to fill and expand the balloon 500, or pushes out stomach juices from inside the inflatable layer 505 to deflate the balloon 500. Though not shown in great detail, the peristaltic pump 525 includes two openings, the inlet opening 515 at the top of the body 520 and an outlet opening (not shown) leading to the space within the inflatable layer 505. Peristaltic rollers 535 of the pump 525 are in fluid connection with flexible tubes that connect to the inlet and outlet openings. In operation, the rollers 535 rotate in one direction to move stomach fluid from one tube to the other tube and out of outlet opening 515, thereby deflating the inflatable balloon device 504. Opposite rotation of the rollers 535 pulls stomach fluid in the inlet opening 515 and expels it to the cavity of the inflatable layer 505, thus inflating the balloon device 504. The inflatable balloon device 504 may further include a control portion or control board 530 and motor (not shown). By inflating the inflatable balloon device 504 to a volume between about 0 milliliters (mL) and about 1000 mL (but preferably between about 400 mL and about 700 mL), the balloon device 504 occupies space in the stomach decreasing the amount of space for food, and also stimulates the stomach walls when the inflatable balloon device 504 (via inflation and/or migration) exerts a pressure on the inner stomach walls.

The rollers 535 may be controlled according to any of a number of methods. Initially, when the inflatable balloon device 504 is first deployed in the patient's stomach, the control board 530 may read a schedule (stored in memory) providing instructions related to the different volumes that inflatable balloon device 504 may adjust to, and at which times. In one example, the schedule may be a daily schedule that the inflatable balloon device 504 follows. Alternatively, the schedule may be for a week, month, year and so forth. After the schedule is read, the target volume may be determined, and the motor may be driven to achieve the target volume. Subsequently, the inflatable balloon device 504 may determine if a trigger to change the volume is detected. For example, the trigger may be merely determining that the schedule dictates a changing of the volume of the inflatable balloon device 504. Other triggers may include a command from an external computer to change the volume of the inflatable balloon device 504.

A portion of the central body 520 of the inflatable balloon device 504 is desirably covered by an antiseptic band 560. The band 560 may be a separate piece of metal attached to the body 520, or may be directly integrated into the body 520 as an exterior layer. The band 560 may be constructed of any material with cleansing, antiseptic qualities. In one example, silver may be used to form the band since silver has natural antiseptic qualities. The function of the band 560 is to passively disinfect the stomach fluid inside the inflatable layer 505.

The insertion process for the inflatable balloon device 504 may be as simple as having the patient swallow the device while in a deflated state. Alternatively, the inflatable balloon device 504 in a deflated state may be carefully inserted through the mouth of the patient, down the esophagus and into the patient's stomach by using a standard grabber.

The removal process for the inflatable balloon device 504 may be substantially the reverse of the insertion process. After substantially deflating the inflatable balloon device 504, a standard grabber may be used to clamp onto one end of the device and pulled back up through the esophagus and out the patient's mouth.

Figure 7:
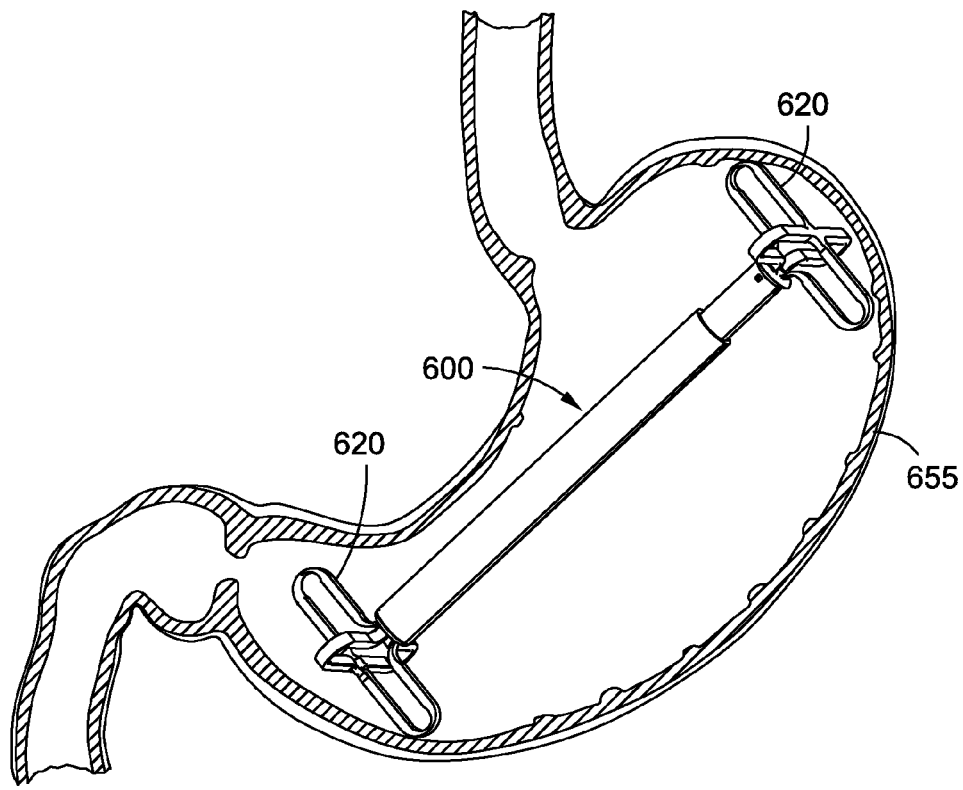
FIG. 7 illustrates a perspective view of an alternative reactive intragastric implant inside a patient's stomach having an elongated spring-biased shaft with soft, folded feet.

FIG. 7 illustrates an alternative reactive intragastric implant 600 implanted inside a patient's stomach in a state exerting pressure on the patient's inner stomach walls. The implant 600 comprises an elongated spring-biased tubular shaft or body 605 with soft, folded atraumatic feet 620 on opposite ends. The tubular body 605 preferably comprises a telescoping structure such that one end 620 attaches to a shaft portion that moves relative to another shaft portion attached to the opposite end, the two shaft portions being spring-biased away from a minimum length. The intragastric implant 600 may reduce appetite as the feet 620 contact and pressure the inside of the patient's stomach walls, thereby affecting nerves and causing early feelings of satiety.

Figure 8:
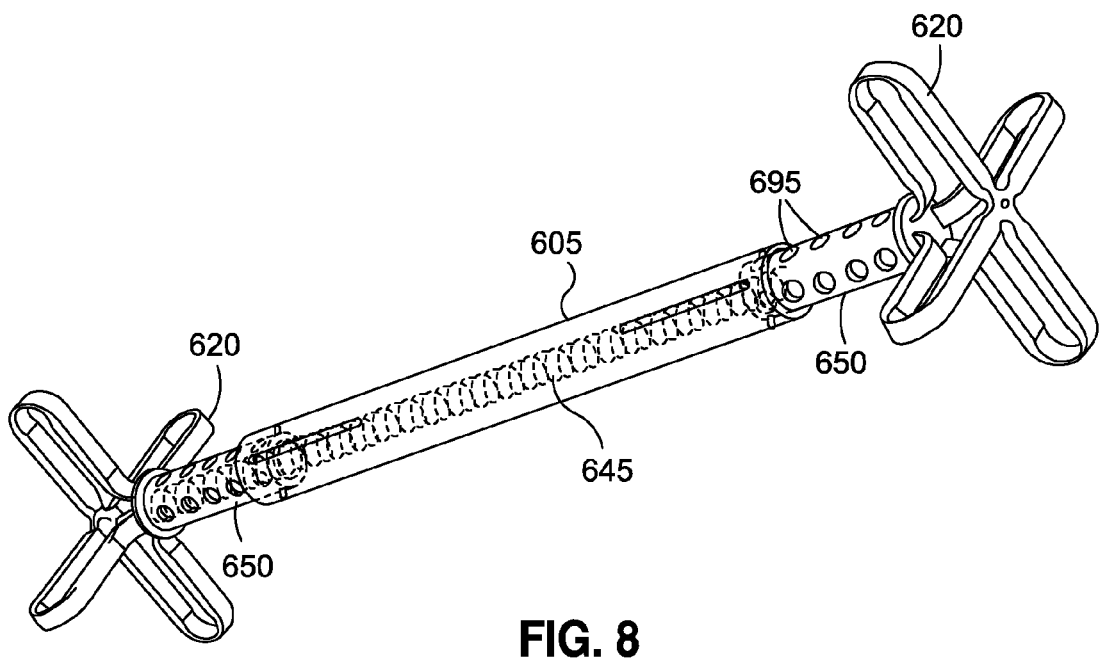
FIG. 8 illustrates a perspective view of the reactive intragastric implant of FIG. 7 showing exemplary spring-biasing structure therein.

The intragastric implant 600 is configured to telescope to varying lengths. For example, FIG. 8 illustrates the intragastric implant of FIG. 7 in an extended position. As shown, extension portions 650 attached to opposite feet 620 are sized smaller than a throughbore of the tubular body 605 and are arranged to slide therein. A spring 645 couples to the extension portions 650 for each foot 620. Inward pressure from the inner stomach walls causes the implant 600 to adjustably telescope to experience a reduction in length. When the extension portions 650 telescope out from within the tubular body 605, the length of the intragastric implant 600 increases. The varying length intragastric implant 600 is desirably reactive in that the size change occurs in reaction to external stomach forces. In one embodiment, a minimum length for the intragastric implant 600 is between about 8-12 cm, while a maximum length is between about 12-15 cm.

Here, no electronics are required. The benefit to this embodiment is that no motor is required (and hence, the production of the implant 600 may be cheaper). However, the trade-off is that the patient's body may have a higher likelihood of compensating to a spring-biased implant 600 since the telescoping depends on the position of the implant and cannot change randomly or according to a diverse schedule. Nevertheless, the action of the reactive intragastric implant 600 is believed to be sufficiently variable to prevent accommodation by the stomach.

The feet 620 may be bent to a straightened or elongated position to allow easier implantation and removal. In embodiment, the entire intragastric implant including the feet 620 (in a straightened state, not shown) may be no larger than 10 millimeters (mm) in diameter, thereby easily passing transorally into the patient's mouth, through the esophagus and into the patient's stomach. However, once implanted inside the patient's stomach, the feet fold to the deployed state as shown in FIGS. 7 and 8. In this state, the feet point outwards and prevent migration through the pylorus, and then the intestines. In another aspect, removal of the reactive intragastric implant 600 may be easily performed using a standard grabber. Once the feet 620 are straightened and the implant 600 is axially compressed, the entire implant 600 may be easily pulled up through the patient's stomach and esophagus and exit the patient's mouth.

The feet 620 are configured to be atraumatic, in that they are soft and pliable. The feet 620 are desirably formed as an array of fingers of a soft polymer, each preferably having thinned regions so as to function like living hinges. More particularly, each of the spokes of the "X" shaped feet 620 has a rectangular cross-section to facilitate bending in one plane, and thinned regions at three points: where it connects to the respective extension portion 650, where it connects to the other spokes along an axis of the device, and at a mid-portion which forms the outermost end of each of the spokes in the deployed configuration seen in FIGS. 7 and 8. When the intragastric implant 600 exerts pressure on the stomach walls the feet 620 bend or flex back toward the tubular body 605. Advantageously, even in this pressuring state, the end portion 620 is not able to migrate through the pylorus. In other words, even at the pressuring state, the foot 620 is still too large to fit through the pylorus. Of course other configurations for the atraumatic feet are contemplated, such as rounded pillows, cups, or the like. Regardless of which embodiment of the reactive intragastric implant 600, the feet 620 may be, for example, an acid-resistant plastic or any other appropriate material injected with radio-opaque additive so that they may be seen with an x-ray machine during the removal procedure.

Furthermore, the tubular body 605 and extension portions 650 are desirably hollow and include through holes 695 to allow stomach juices to flow through. The tubular body 605 and extension portions 650 may be constructed, for example, out of a polysulphone, polypropylene or an acid-resistant plastic material configured to resist the strong acidity of the stomach juices.

Figure 9C:
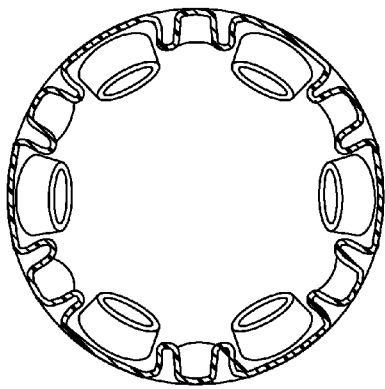
Figure 10C:
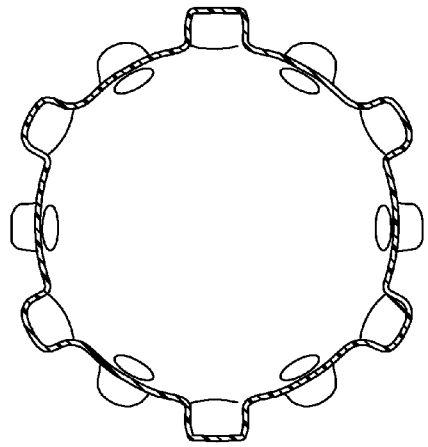
FIGS. 10A-10C are equivalent views with the pop-out surface features in extended positions.
Figure 9B:
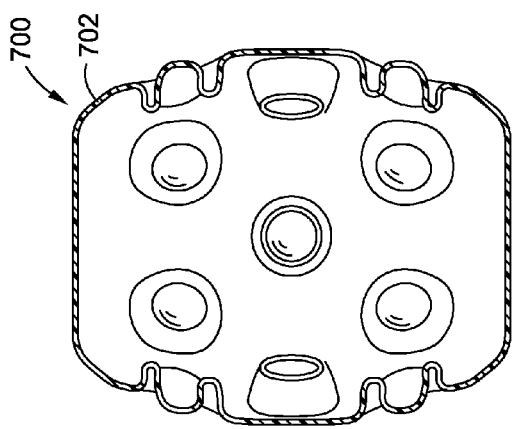
Figure 10B:
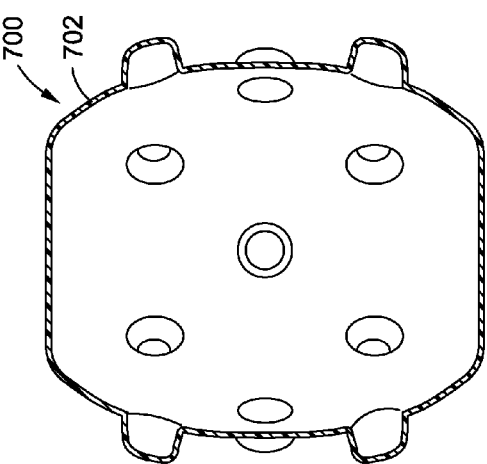
Figure 9A:
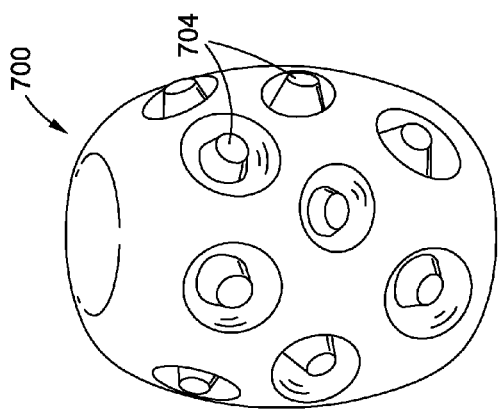
Figure 10A:
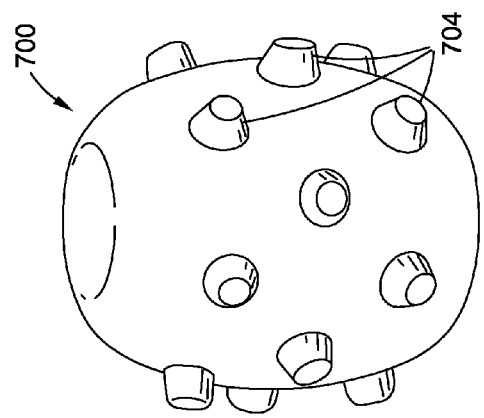

FIGS. 9A-9C illustrates an alternative reactive intragastric implant 700 comprising a generally barrel-shaped inflatable member 702 having a multiplicity of "pop-out" surface features 704 on its surface that reside generally flush with the inflatable body in relaxed, retracted states, and which respond to an increase in pressure within the inflatable body by projecting outward from the body in a stressed, deployed state. The popout surface features 704 as illustrated are small circular dimples in the wall of the inflatable member provided in three rows spaced along an axis of the inflatable member 702. In one embodiment, the surface features 704 in the middle row are offset from those in the top and bottom rows. Of course, other patterns and spacing of the surface features 704 are possible. FIGS. 10A-10C are equivalent views with the pop-out surface features 704 in extended positions, wherein they form outwardly projecting cylinders from the remainder of the substantially barrel-shaped inflatable member 702.

Figure 11C:
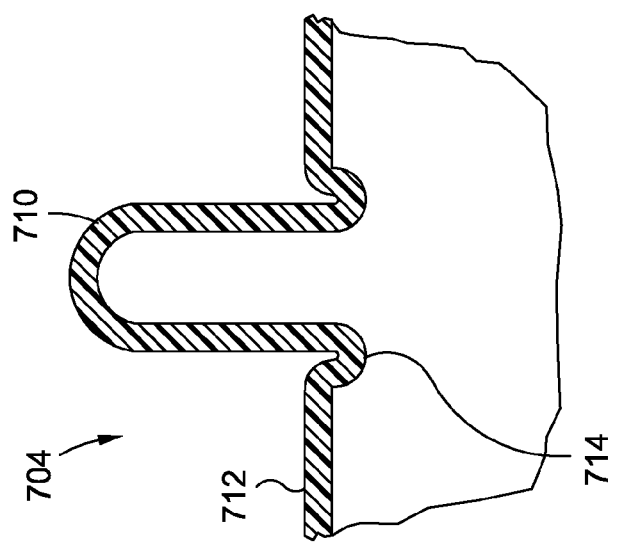
FIGS. 11A-11C are sectional views through one of the pop-out surface features illustrating a preferred rolling diaphragm wall structure enabling movement from the retracted to the extended position.
Figure 11B:
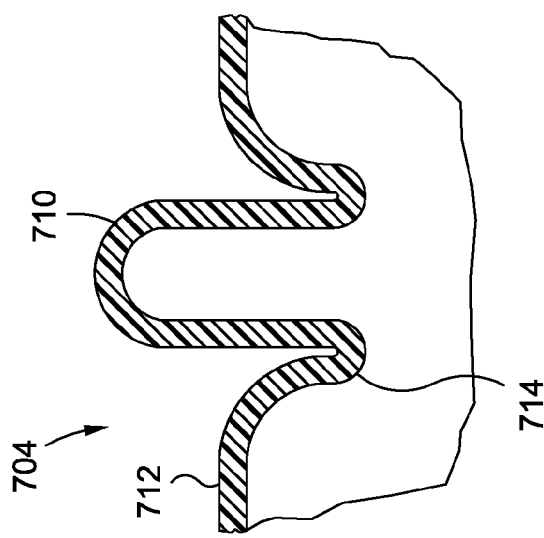
Figure 11A:
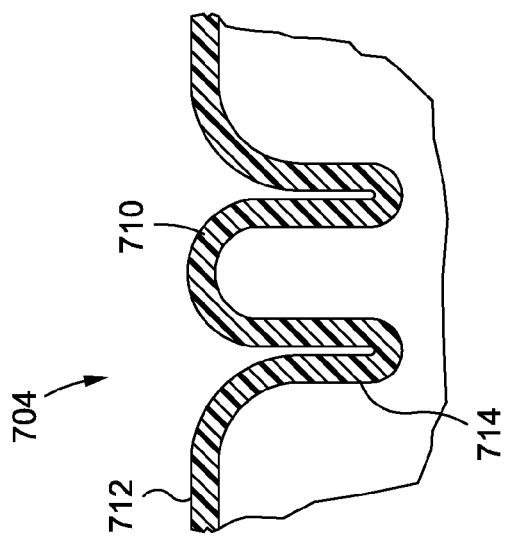

FIGS. 11A-11C are sectional views through one of the pop-out surface features 704 illustrating a preferred rolling diaphragm wall structure. That is, each surface features 704 in its retracted position of FIG. 11A includes a cylindrical portion 710 that connects to the surrounding flat wall portion 712 via a 360° rolling diaphragm 714. As pressure within the inner chamber of the inflatable number 702 increases, the cylindrical portion 710 begins to project from the surrounding wall portion 712 as seen in FIG. 11B. This occurs by virtue of the rolling diaphragm 714, which gradually transitions to become a part of the side of the cylindrical portion 710. Finally, in FIG. 11C, the cylindrical portion 710 projects outward from the wall portion 712 a maximum distance, and the rolling diaphragm 714 is at its minimum length. Of course, a reduction in pressure within the inner chamber of the inflatable member 702 causes a reverse action, by virtue of the elasticity of the rolling diaphragm 714. That is, the "as-molded" shape of each surface feature 704 is as shown in FIG. 11A, such that the default position is that in which the cylindrical portion 710 is retracted to be approximately level with the surrounding wall portion 712.

Figure 12C:
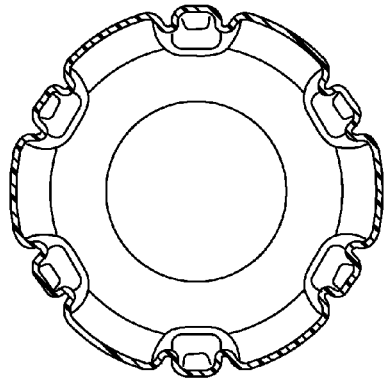
Figure 13C:
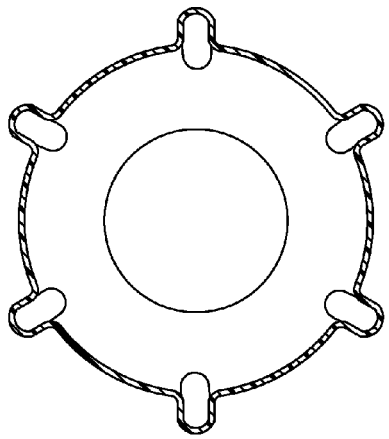
FIGS. 13A-13C show the elongated pop-out surface features in extended positions.
Figure 12B:
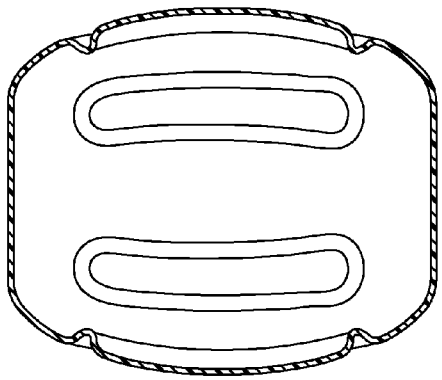
Figure 13B:
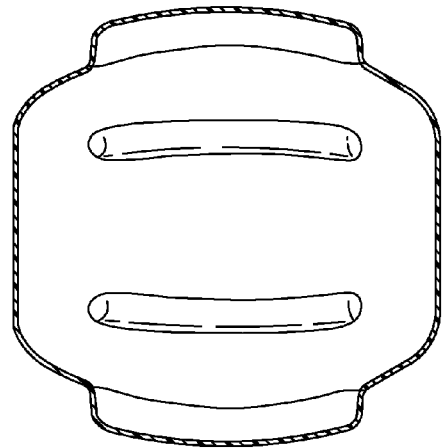
Figure 12A:
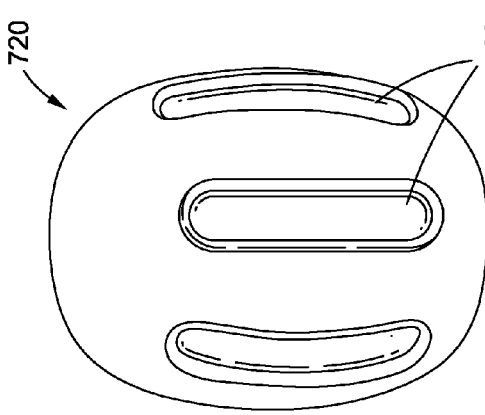
Figure 13A:
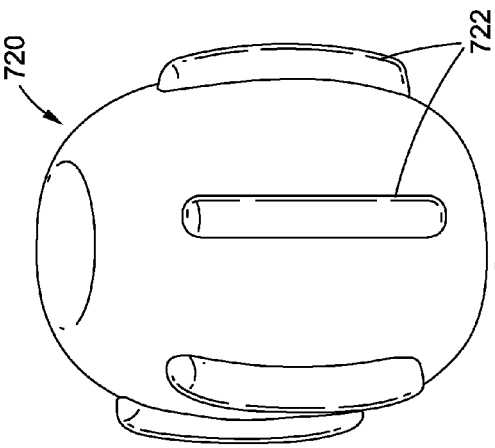

FIGS. 12A-12C illustrates a further barrel-shaped inflatable intragastric implant 720 having elongated "pop-out" surface features 722 in retracted positions, while FIGS. 13A-13C show the elongated pop-out surface features in extended positions. In this configuration, there are a total of six elongated surface features 722 arranged equidistantly around the circumference of the implant 720, and centrally positioned along its axis. The surface features 722 desirably function the same as described above, with rolling diaphragms permitting the bar shaped elements to ultimately project and retract relative to the surrounding wall portions. Indeed, the sectional views of FIGS. 11A-11C equally represent a horizontal section through one of the bar-shaped surface features 722, at least away from its ends.

The intragastric implants 700, 720 described above are primarily volume occupying, similar to current gastric balloons. As such, the fill volume is desirably the same, preferably between 400-700 mL. However, because of the popout surface features, the implants also provide enhanced stimulation to the surrounding stomach walls, which induces satiety. Furthermore, a number of rotationally variant intragastric implants are shown below with reference to FIGS. 16-17, and the popout features could easily be incorporated therein to provide further stimulation to the stomach walls.

The two embodiments of intragastric implants 700, 720 with popout features 704, 722 shown in FIGS. 9-13 are exemplary only, and numerous other configurations are contemplated. For example, the above features are shown as being evenly distributed over the surface of the implants, while in the alternative the features can be randomly distributed. Also, the polar ends of the barrel-shaped implant 700, 720 are shown absent of the popout features, though they can be provided all over the devices. Likewise, the shape of the projecting popout features 704, 722 are relatively rounded; domed cylindrical in the first embodiment and half tubular in the second. However, more angular or pointed shapes can be molded into the walls of intragastric implants and surrounded by rolling diaphragms so that the resulting projections are somewhat more stimulating to the inner walls of the stomach.

Finally, a "rolling diaphragm" refers to a region surrounding each of the popout features that permits a projection to remain retracted until an inner chamber of the implant is pressurized, at which time it extrudes out from the surrounding wall surfaces. The illustrated embodiment of rolling diaphragm shows a continuous transition of the diaphragm which "rolls" at a crease. Another way to define rolling diaphragm is a surface feature that allows for a change in the outer surface shape without any change in surface area. These intragastric implants experience bending stresses to change shape, rather than experiencing tensile stretching, which improve the durability of the devices. The same function can be obtained with structure that is more hinged as opposed to rolling, such that there is a sudden transition between a retracted position to a projecting position. Additionally, other popout configurations include a folded or spiral shape that unfolds when pressurized, elements that lie flat against the wall of the implant until pressurized, thinned regions of the wall which bow outward from surrounding figure wall portions, etc. It should be understood that the term "popout features" encompasses all of these variations.

Figure 14:
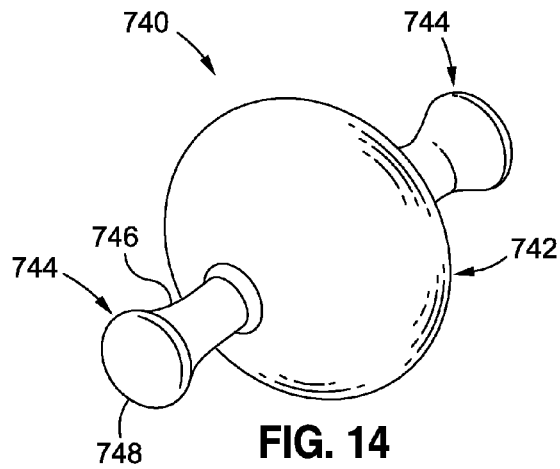
FIG. 14 illustrates another a reactive intragastric implant comprising an underfilled inflatable member having outer wings that transition between floppy to stiff configurations.

FIG. 14 illustrates a still further reactive intragastric implant 740 comprising an underfilled central inflatable member 742 having outer wings 744 that transition between floppy to stiff configurations. The entire implant 740 defines a single fluid chamber therein. In the illustrated embodiment, the inflatable member 742 is substantially spherical, while the outer wings 744 resemble stems with a narrow proximal shaft 746 terminating in a bulbous head 748. Also, a pair of the outer wings 744 extend from opposite poles of the spherical inflatable member 742, which is believed to facilitate alignment of the implant 740 within the stomach, though more than two such wings distributed more evenly around the inflatable member could be provided.

Figure 15A:
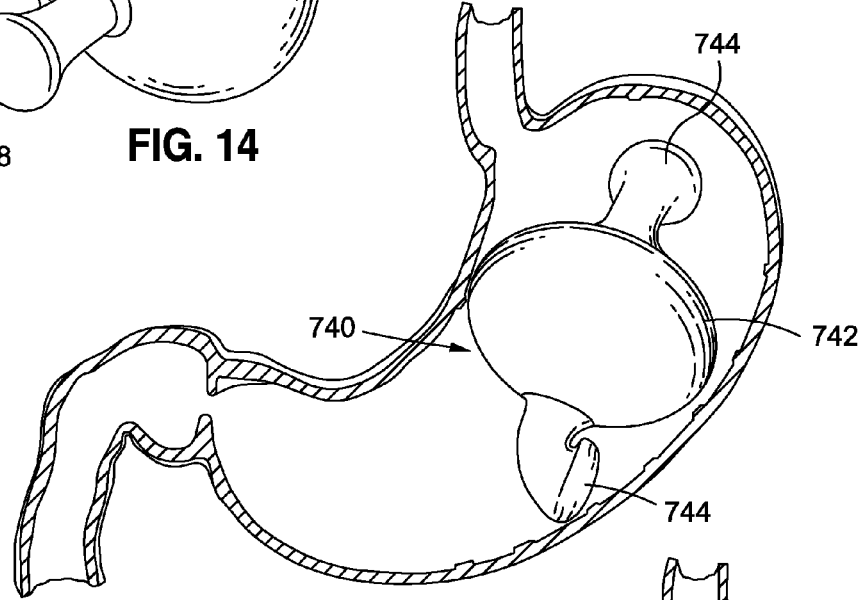
FIGS. 15A-15B show the intragastric implant of FIG. 14 implanted in the stomach in both relaxed and squeezed states, showing the transition of the outer wings between floppy and stiff configurations.
Figure 15B:
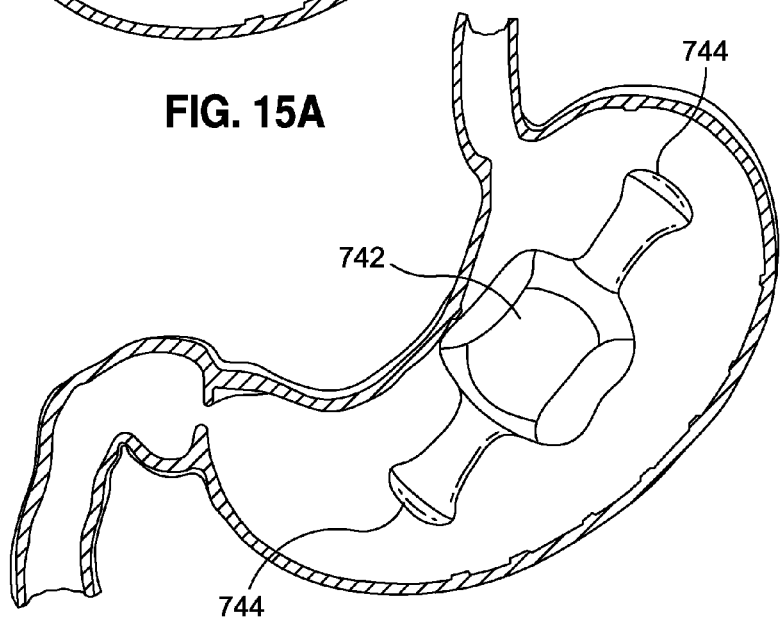

FIG. 15A shows the intragastric implant 740 implanted in the stomach in a relaxed state, while FIG. 15B shows the implant in a squeezed state, illustrating the transition of the outer wings 744 between floppy and stiff configurations. The shape of the central inflatable member 742 in FIG. 15B is a representation of the shape as if squeezed by the surrounding stomach walls, however the illustrated stomach is shown in its relaxed configuration. Transition between the relaxed and squeezed state of the implant 740 occurs when the stomach walls squeeze the central inflatable member 742, thus pressurizing the outer wings 744. In other words, fluid is driven from the central member 742 and into the outer wings 744. In a certain sense, the outer wings 744 function similar to the popout features, though they are always external to the central inflatable member 742.

Initially, the entire implant 740 is underfilled with a fluid such as saline or air to a degree that the wings 744 are floppy, and a predetermined compressive force causes them to become stiff. For example, the fully filled volume of the intragastric implant 740 may be between 400-700 mL, though the implant is filled with less than that, thus providing slack for flow into the wings 744. Additionally, it should be noted that underfilling the implant 740 results in lower stresses within the shell wall, which may improve the degradation properties of the material within the stomach's harsh environment.

Figure 16:
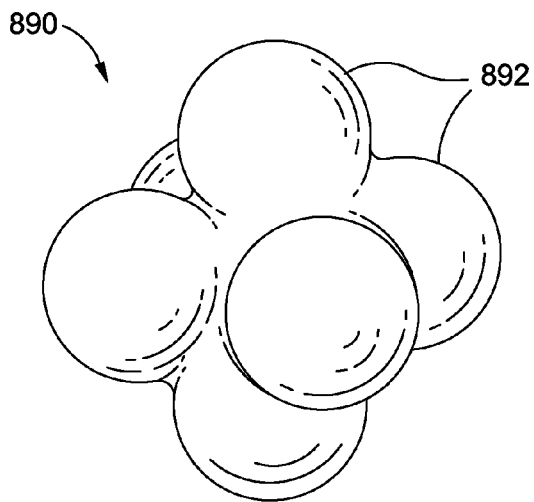
FIGS. 16 and 17 illustrate intragastric devices that encourage rotational variation.
Figure 17:
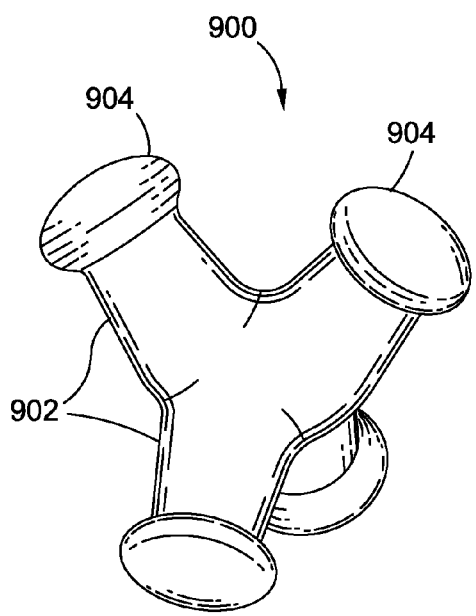

FIGS. 16 and 17 illustrates certain specific features that may encourage rotational variation. In FIG. 16, an intragastric obesity treatment device 890 essentially comprises an aggregation of spheres 892. The overall exterior shape of the device is somewhat spherical, encouraging rotation. However, the outwardly projecting spheres that make up the device contact the stomach wall at different locations as the device rotates. In FIG. 17, a device 900 comprises a plurality of outwardly projecting legs 902 terminating in rounded or bulbous feet 904. Again, the device 900 rotates relatively easily within the stomach, especially upon peristaltic motion, and the separated legs 902 and feet 904 therefore contact the stomach wall at different locations on a constantly changing basis. These features can be utilized in a device that looks like the device 900, or can be added to the number of the embodiments described herein, such as the inflated balls of FIGS. 8 and 10.

The devices 890, 900 of FIGS. 16 and 17 may also serve to temporarily block the pylorus and slow gastric emptying. Consequently, such protrusions as the spheres 892 and bulbous feet 904 may be added to a number of the devices described herein.

Figure 18:
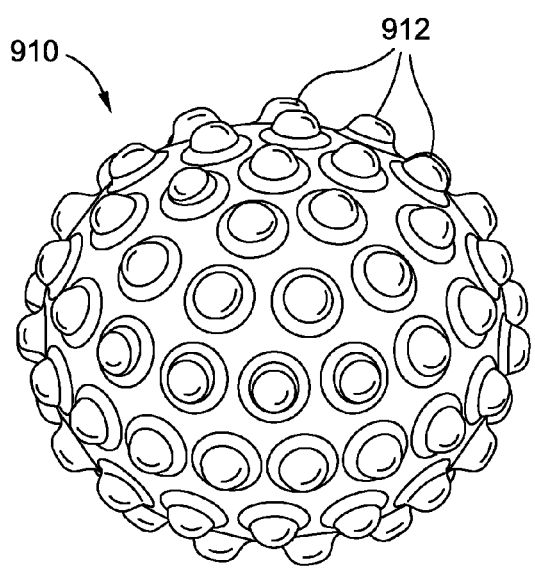
FIGS. 18 and 19 illustrate intragastric devices that both encourage rotational variation and provide additional stomach cavity stimulation.
Figure 19:
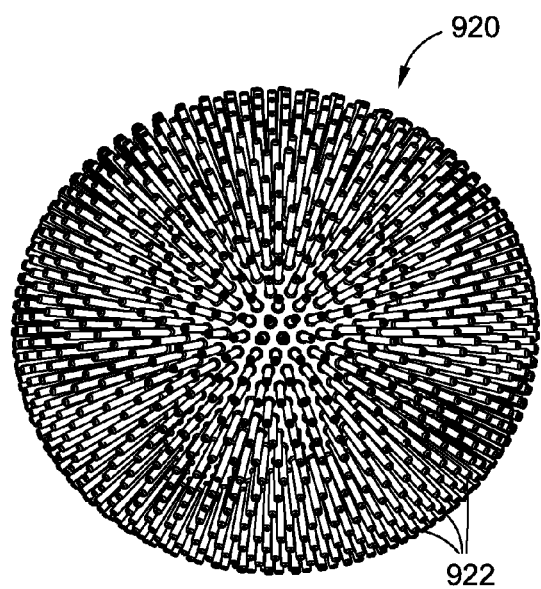

Another option for a number of the intragastric devices disclosed herein is to add exterior stimulation features, such as any raised or depressed geometry which act to stimulate certain portions of the stomach walls. Such features may be particularly effective for those embodiments which stimulate the cardia. For instance, FIG. 18 illustrates a spherical intragastric device 910 having numerous external bumps 912 projecting outward therefrom. These bumps 912 separately contact the inner walls of the stomach, potentially increasing the stimulation to the surrounding satiety-sensing nerves. Another example of exterior stimulation features is seen in FIG. 19, where an intragastric device 920 formed as a sphere features a multitude of small flagella 922 extending outward therefrom. It should be noted that the two embodiments shown in FIGS. 18 and 19 rotate freely within the stomach, and that the bumps 912 or flagella 922 may be provided in a non-uniform distribution so as to take advantage of the benefits of the rotational variation described above. That is, a regular array of such exterior features may stimulate the stomach wall more than a smooth surface, but also providing a non-uniform distribution will create different sensations on a constantly changing basis.

It should also be stated that any of the embodiments described herein may utilize materials that improve the efficacy of the implant. For example, a number of elastomeric materials may be used including, but not limited to, rubbers, fluorosilicones, fluoroelastomers, thermoplastic elastomers, or any combinations thereof. The materials are desirably selected so as to increase the durability of the implant and facilitate implantation of at least six months, and preferably more than 1 year.

Material selection may also improve the safety of the implant. Some of the materials suggested herein, for example, may allow for a thinner wall thickness and have a lower coefficient of friction than the implant.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:

Silicone materials used include 3206 silicone for any shells, inflatable structures, or otherwise flexible hollow structures. Any fill valves will be made from 4850 silicone with 6% $BaSo_4$. Tubular structures or other flexible conduits will be made from silicone rubber as defined by the Food and Drug Administration (FDA) in the Code of Federal Regulations (CFR) Title 21 Section 177.2600.

Purposes:

the devices are for human implant, the devices are intended to occupy gastric space while also applying intermittent pressure to various and continually changing areas of the stomach;

the devices are intended to stimulate feelings of satiety, thereby functioning as a treatment for obesity.

General Implant Procedures:

The device is intended to be implanted transorally via endoscope into the corpus of the stomach.

Implantation of the medical devices will occur via endoscopy.

Nasal/Respiratory administration of oxygen and isoflurane to be used during surgical procedures to maintain anesthesia as necessary.

One exemplary implant procedure is listed below.

a) Perform preliminary endoscopy on the patient to examine the GI tract and determine if there are any anatomical anomalies which may affect the procedure and/or outcome of the study.

b) Insert and introducer into the over-tube.

c) Insert a gastroscope through the introducer inlet until the flexible portion of the gastroscope is fully exited the distal end of the introducer.

d) Leading under endoscopic vision, gently navigate the gastroscope, followed by the introducer/over-tube, into the stomach.

e) Remove gastroscope and introducer while keeping the over-tube in place.

f) OPTIONAL: Place the insufflation cap on the over-tubes inlet, insert the gastroscope, and navigate back to the stomach cavity.

g) OPTIONAL: Insufflate the stomach with air/inert gas to provide greater endoscopic visual working volume.

h) Collapse the gastric implant and insert the lubricated implant into the over-tube, with inflation catheter following if required.

i) Under endoscopic vision, push the gastric implant down the over-tube with gastroscope until visual confirmation of deployment of the device into the stomach can be determined.

j) Remove the guide-wire from the inflation catheter is used.

k) If inflated: Inflate the implant using a standard BioEnterics Intragastric Balloon System ("BIB System") Fill kit.

l) Using 50-60 cc increments, inflate the volume to the desired fill volume.

m) Remove the inflation catheter via over-tube.

n) Inspect the gastric implant under endoscopic vision for valve leakage, and any other potential anomalies. Record all observations.

o) Remove the gastroscope from over-tube.

p) Remove the over-tube from the patient.

End Point Criteria:

Weight Loss

Comprehensive Metabolic Panel (CMP)

HbA1C

Lipid Panel

Tissue Samples/Response

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A reactive implantable device configured to be placed in a patient's stomach transorally without surgery to treat and prevent obesity by applying a pressure to the patient's stomach, comprising:
   an inflatable body having an internal volumetric capacity of between 400-700 ml and being made of a material that permits it to be compressed into a substantially linear transoral delivery configuration and that will resist degradation over a period of at least six months within the stomach, the body having an outer surface on which a plurality of popout features reside, the popout features extending from a radially outer end to a radially inner end, the radially outer end being flush with the surface of the body and the radially inner end being recessed below the surface of the body in a relaxed, retracted state, and the radially outer end being radially spaced outwardly from the surface of the body in a stressed, deployed state, wherein the popout features transition from the retracted state to the deployed state in response to an increase in pressure within the inflatable body, and the popout features transition from the deployed state to the retracted state automatically in response to a decrease in pressure within the inflatable body, the popout features having a same surface area in each of the retracted and deployed states.

2. The device of claim 1, wherein the inflatable body has a generally barrel shape along an axis.

3. The device of claim 2, wherein the popout features are generally cylindrical.

4. The device of claim 2, wherein the popout features are rounded bars oriented parallel to the axis.

5. The device of claim 1, wherein the popout features convert between their retracted and deployed states by movement of rolling diaphragms formed in the inflatable body.

6. An implantable device configured to be placed in a patient's stomach transorally without surgery to treat and prevent obesity by applying a pressure to the patient's stomach, comprising:
   an inflatable body having an internal volumetric capacity of between 400-700 ml and being made of a material that permits it to be compressed into a reduced diameter transoral delivery configuration and that will resist degradation over a period of at least six months within the stomach, the body having an outer surface on which a plurality of popout features reside, the popout features extending from a radially outer end to a radially inner end, the radially outer end being flush with the surface of the body and the radially inner end being recessed below the surface of the body in a relaxed, retracted state, and the radially outer end being radially spaced outwardly from the surface of the body in a stressed, deployed state, wherein the popout features transition from the retracted state to the deployed state in response to an increase in pressure within the inflatable body, and the popout features transition from the deployed state to the retracted state automatically in response to a decrease in pressure within the inflatable body, wherein the popout features comprise a rolling diaphragm structure in the surface upon which the popout features move between the retracted and deployed states.

7. The device of claim 6, wherein the inflatable body is substantially barrel-shaped.

8. The device of claim 7, wherein wherein the popout features are defined as dimples in an exterior wall of the inflatable body.

9. The device of claim 8, wherein wherein the dimples are provided in a plurality of rows spaced along an axis of the inflatable body.

10. The device of claim 9, wherein wherein the dimples in adjacent rows are radially offset from each other.

11. The device of claim 7, wherein the popout features form outwardly projecting cylinders from the remainder of the inflatable body.

12. The device of claim 6, wherein the popout features include a projection that remains retracted until an inner chamber of the inflatable body is pressurized, at which time the popout features extrudes out from its surrounding wall surfaces.

13. The device of claim 6, wherein the popout features each define a 360° crease about which the popout features roll into respective projected shapes relative to the inflatable body.

14. The device of claim 6, wherein the popout features extend longitudinally along an axis of the inflatable body.

15. The device of claim 14, wherein the popout features are rounded bars oriented parallel to the axis.

16. The device of claim 6, wherein the popout features are generally cylindrical.

17. The device of claim 6, wherein the popout features having a same surface area in each of the retracted and deployed states.

* * * * *